United States Patent
Falb et al.

[11] Patent Number: 5,243,973
[45] Date of Patent: Sep. 14, 1993

[54] METERING DEVICE FOR A LIQUID ANESTHETIC VIA AN INTERMEDIATE CONTAINER

[75] Inventors: Wolfgang Falb, Krummesse; Karl-Ludwig Gippert; Ulrich Heim, both of Lübeck; Uvo Hölscher, Stockelsdorf; Siegfried Kiske, Koümmesse; Götz Kullik, Lübeck; Ralf-Ernst Löser, Kreuzkamp; Christoph Maurer, Bad Schwartau, all of Fed. Rep. of Germany

[73] Assignee: Dragerwerk Aktiengesellschaft, Lubeck, Fed. Rep. of Germany

[21] Appl. No.: 833,298

[22] Filed: Feb. 10, 1992

[30] Foreign Application Priority Data

Mar. 6, 1991 [DE] Fed. Rep. of Germany ....... 4107060

[51] Int. Cl.⁵ .............................................. A61M 16/00
[52] U.S. Cl. .......................... 128/203.27; 128/203.25; 128/203.12; 137/393
[58] Field of Search ...................... 128/203.12, 203.17, 128/203.26, 203.27, 203.25, 202.22; 137/393

[56] References Cited

U.S. PATENT DOCUMENTS

| | | | |
|---|---|---|---|
| 3,351,057 | 11/1967 | Goodyear | 128/202.22 |
| 3,873,806 | 3/1975 | Schossow | 219/273 |
| 4,300,131 | 11/1981 | Mitsui | 340/618 |
| 4,303,601 | 12/1981 | Grimm | 261/142 |
| 4,484,576 | 11/1984 | Albarda | 128/202.22 |
| 4,587,966 | 5/1986 | Albarda | 128/202.22 |
| 4,606,866 | 8/1986 | McGlothlin | 261/74 |
| 4,750,483 | 6/1988 | Ankartross | 128/203.26 |
| 4,770,168 | 9/1988 | Rusz | 128/203.12 |

FOREIGN PATENT DOCUMENTS

| | | | |
|---|---|---|---|
| 59210 | 4/1982 | Japan | 137/393 |
| 125210 | 4/1919 | United Kingdom | 128/203.12 |
| 2176313 | 12/1986 | United Kingdom | 128/203.12 |

Primary Examiner—Edgar S. Burr
Assistant Examiner—Eric P. Raciti
Attorney, Agent, or Firm—McGlew and Tuttle

[57] ABSTRACT

A metering device for a liquid anesthetic that is fed from a reservoir via a supply line into a heatable intermediate container maintained under pressure, from which gaseous anesthetic is fed via a metering valve into a fresh gas line. Accurate metering, which can be better monitored, is provided for low-boiling anesthetics. A supply unit 7 is mounted in the supply line 5, and liquid anesthetic is transported by the supply unit 7 into the intermediate container 6 until it is filled up to a predetermined filling level. A heating device 12 stabilizes the temperature of the liquid bath and ensures a sufficiently high vapor pressure of the gaseous anesthetic above the liquid phase. The anesthetic vapor is sent via the metering valve into the fresh gas line.

10 Claims, 1 Drawing Sheet

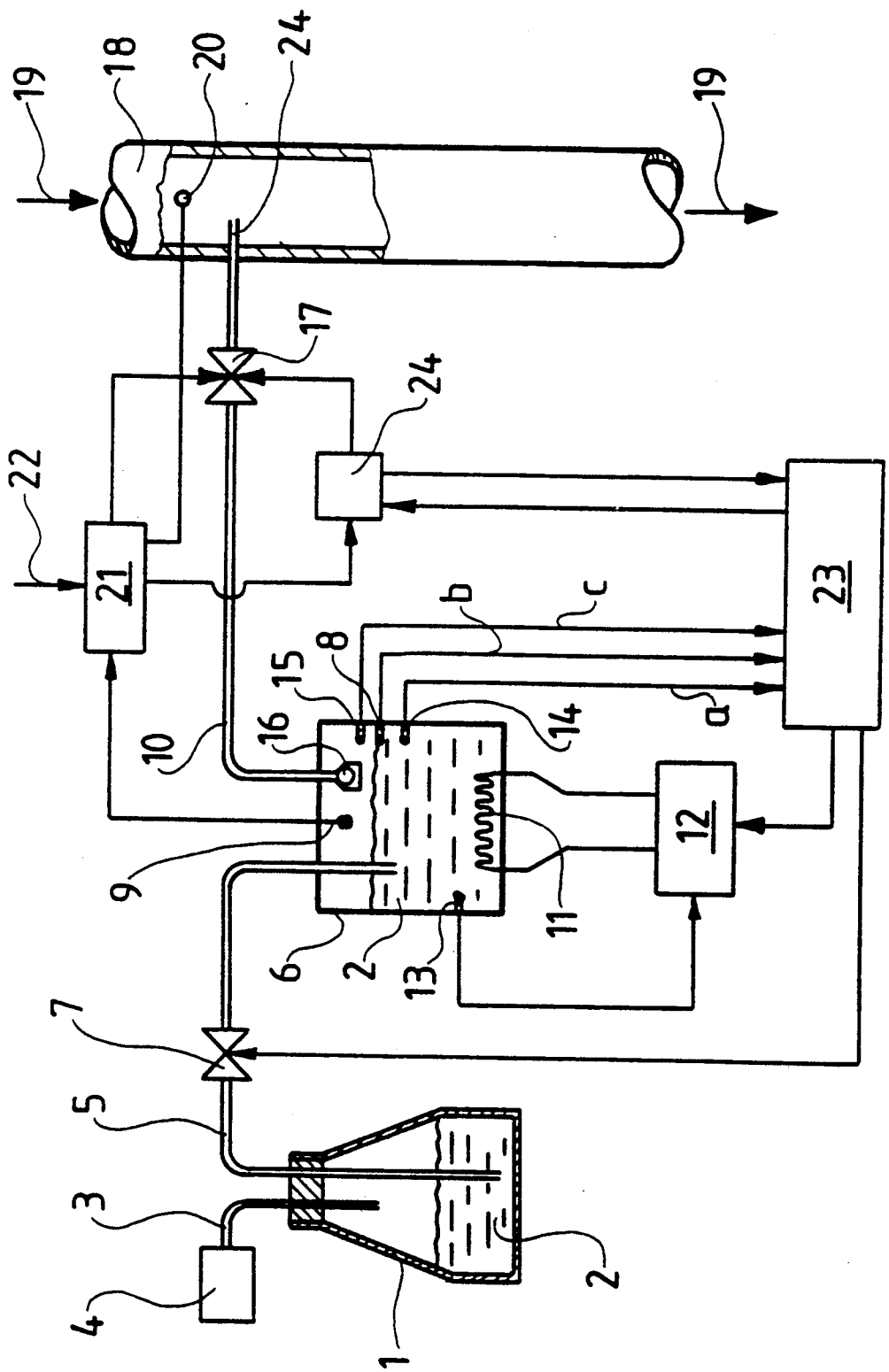

METERING DEVICE FOR A LIQUID ANESTHETIC VIA AN INTERMEDIATE CONTAINER

FIELD OF THE INVENTION

The present invention pertains to a metering device for a liquid anesthetic and more particularly to a metering device in which liquid anesthetic is fed from a reservoir via a supply line into a heatable intermediate container maintained under a preselectable pressure, whose outlet line carries the anesthetic, which is brought to the vapor state by the heating device, into a fresh gas line via a metering valve.

BACKGROUND OF THE INVENTION

Such a metering device has become known from EP-A-2-231,513. This prior-art anesthetic metering device consists of a reservoir, from which liquid anesthetic is pressed into a heated intermediate container by a delivery pressure. The heating temperature and the internal pressure of the intermediate container are adjusted to one another so that the liquid anesthetic evaporates immediately after entry into the intermediate container and occurs in this only as a gaseous anesthetic. Via a cyclically operating metering valve in the outlet line, the pressurized anesthetic vapor is fed into a carrier gas line, through which, e.g., an oxygen-laughing gas mixture is sent to an anesthetic apparatus. Corresponding to the vapor pressure in the intermediate container, the degree of opening of the metering valve and the volume flow of the carrier gas per unit time, a corresponding anesthetic concentration value becomes established in the carrier gas stream.

One disadvantage of the prior-art anesthetic metering device is the fact that in the case of insufficient heating of the intermediate container or malfunction of the heating device, liquid anesthetic may enter the carrier gas stream and lead to a considerable, undesired increase in concentration there. Liquid anesthetic may enter the carrier gas stream especially if the metering valve is jammed in the open state due to a malfunction. Another disadvantage is the fact that complicated means are required for a simple control of the amount of liquid anesthetic that is delivered into the intermediate container from the reservoir and evaporates in it the intermediate container. Even a slight change in the amount of anesthetic delivered from the reservoir into the intermediate container leads to a drastic change in the vapor pressure at a given temperature there.

In the prior-art metering device, the pressure of the evaporated anesthetic in the intermediate container is exactly equal to the delivery pressure in the reservoir. Therefore, this pressure must be exactly preset in a complicated manner. In the case of low-boiling anesthetics, which boil even at room temperature, this pressure control in the reservoir is extremely difficult, because the vapor pressure that develops may be on the same order of magnitude as the desired delivery pressure.

SUMMARY AND OBJECTS OF THE INVENTION

It is an object of the present invention to improve a metering device of the above-described type so that an accurate, easy-to-monitor possibility is provided for metering, especially for low-boiling anesthetics.

This task is accomplished by providing, in the supply line, a supply unit which allows, via a control unit, the liquid anesthetic to flow into the intermediate container until a predetermined filling level set value of liquid anesthetic is reached in it, and by the heating device heating the liquid anesthetic to such a temperature that gaseous anesthetic under the predetermined pressure will occur above the liquid level.

The advantage of the present invention essentially lies in the fact that, as a consequence of the intermediate storage of liquid anesthetic in the heatable intermediate container and by regulating the liquid temperature, the vapor pressure that is relevant for the accuracy of metering is determined directly in the intermediate container, rather than depending on a delivery pressure in the reservoir, which is difficult to control, especially in the case of low-boiling anesthetics. Furthermore, monitoring of the filling level in the intermediate container makes it possible to redundantly monitor the amount of anesthetic to be delivered from the reservoir. For monitoring, the control unit receives the corresponding filling level value from a filling level indicator via a filling level signal line, and this filling level value can then be used for further processing and display.

In the general case, a supply unit is defined as a delivery device that delivers the liquid anesthetic from the reservoir into the intermediate container. In a simple case, this may be a pump, or it is a simple feed valve, which allows, in the open state, the liquid anesthetic to flow freely into the intermediate container from the reservoir that is under excess pressure.

The filling level of the liquid anesthetic in the intermediate container is preferably monitored so that a minimum filling level indicator, whose minimum value signal is sent to the control unit via a signal line, is provided, and if the minimum value signal is present, the feed valve is kept open by the control unit until the filling level set value is reached. The liquid level of the anesthetic in the intermediate container, which fluctuates between the minimum filling level and the filling level set value, is the only magnitude to be monitored in this embodiment which is to be determined by the control unit. The pressure in the gaseous phase above the liquid level within the intermediate container may become established automatically in the case of liquid anesthetics with correspondingly low boiling points, or it is generated and maintained by a controlled heating device in the case of higher-boiling liquids, wherein the fluctuating anesthetic liquid level between the filling level set value and the minimum value is irrelevant for this.

If monitoring of the filling level set value is defective in case of a malfunction, it is useful to provide a maximum filling level indicator whose maximum value signal can be sent via a monitoring line to the control unit, and if the maximum value signal is present, the control unit will bring the supply unit and the metering valve to the closed position.

The amount of gaseous anesthetic to be metered from the intermediate container into the anesthetic gas line may be adjusted and monitored in a simple manner by providing a metering control that detects the flow in the fresh gas line by means of a flow sensor and the vapor pressure of the gaseous anesthetic in the intermediate container by means of a pressure sensor, and determines the switching cycles of the metering valve on the basis of the calculated amount of anesthetic to be dosed that is necessary to reach a predetermined anesthetic concentration value. To achieve this, the flow sensor, calibrated to detect the volume flow, sends its measured flow value to the metering control, in which the amount of anesthetic necessary to produce a defined set value of anesthetic concentration in the fresh gas will then be calculated. Corresponding to the pressure occurring in the intermediate container, which can be measured, e.g., by means of a pressure sensor or calculated by the control unit on the basis of the temperature of the liquid anesthetic based on the vapor pressure curve of the anesthetic, the metering control will actuate the metering valve so that the required amount of anesthetic will flow through the outlet line into the fresh gas line. The metering valve may be an analog valve of variable cross section or a digital valve cycled between its open position and its closed position. The amount of anesthetic flowing through is determined by the opening cross section in one case, and by the cycle time ratio between the closed state and the open state in the second. An additional safety monitoring of the necessary quantity of anesthetic determined can be performed in a simple manner by the control unit calculating the quantity of anesthetic consumed from the number of filling cycles per unit time between the minimum filling level indicator and the filling level indicator, comparing it in a comparison unit with the amount of anesthetic determined by the metering control, switching off the supply unit in the case of a deviation between the two by an amount exceeding a predetermined difference value, bringing the metering valve to the closed position, and turning off the heating device. Even if the deviation between the quantities of anesthetic determined by the metering control and the control unit is due to jamming of the metering valve in the open position, only the small amount of anesthetic vapor reserve in the intermediate container will be released into the carrier gas.

In all embodiments of the present invention, the external excess pressure acting on the reservoir for delivery of the liquid anesthetic into the intermediate container is no longer decisive for the accuracy of delivery, because, unlike in the case of the state of the art, this excess pressure does not directly affect the accuracy of metering any longer. Only one condition, which is easy to satisfy, needs be met: the pressure gradient between the reservoir and the intermediate container must be great enough to overcome the excess pressure set in the intermediate container. The temperature in the intermediate container, which is thermally insulated from the environment, is preferably selected so that the pressure in the intermediate container will be a few 100 mbar above the normal pressure. At the same time, the temperature should preferably be higher than the highest possible operating temperature. In the case of an anesthetic boiling at room temperature, such a temperature is ca. 33° C., which would lead to a vapor pressure ca. 700 mbar above normal pressure in the intermediate container.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE is a schematic representation of the metering device according to the invention.

DETAILED DESCRIPTION OF THE PREFERRED EMBODIMENT

The only FIGURE shows a pressure-resistant reservoir vessel 1 for a low-boiling liquid anesthetic 2, which vessel 1 is connected to a compressed gas source 4 via a compressed gas line 3 in order to maintain a pressure above the liquid anesthetic level, as a result of which the anesthetic 2 is fed into an intermediate container 6 via a supply line 5. A supply unit 7, which is represented as an on-off valve that can be actuated electromagnetically, is located in the supply line section 5. The pressure-resistant intermediate container 6 is partially filled with the anesthetic 2, whose liquid level has risen up to a filling level indicator 8. The intermediate container 6 also contains a pressure sensor 9, the admission opening of an outlet line 10, as well as an electrical heating coil 11 supplied by a heating device 12; furthermore, a temperature sensor 13 is also located within the liquid anesthetic. A minimum filling level indicator 14 is arranged beneath the filling level indicator 8 and a maximum filling level indicator 15 is arranged above indicator 8. The filling level indicators 8, 14, 15 are designed as capacitive measuring sensors which have two sensor electrodes, not shown, by which a capacitive measured signal is generated; this capacitive measured signal will change as soon as these measuring sensors are covered with liquid anesthetic. The outlet line 10 is provided with a float valve 16. In the further course of the outlet line 10, there is a metering valve 17, whose outlet opens into a fresh gas line 18, which is represented only partially and through which an oxygen-laughing gas mixture flows as a carrier gas along the direction arrows 19. A flow sensor 20 within the fresh gas line 18 is connected to a metering control 21. The metering control 21 also receives a signal from the pressure sensor 9. A set value input 22 for the anesthetic concentration in the fresh gas line is also provided on the metering control 21. A control unit 23 monitors and controls the processes in conjunction with anesthetic delivery from the reservoir 1 into the intermediate container 6, as well as the heater 12 and the filling level indicators 8, 14, 15. The link between the metering control 21 and the control unit 23 is formed by a comparison unit 24.

A metering process will be explained below on the basis of the figure. In the state shown, the level of the liquid anesthetic 2 in the intermediate container 6 is at its filling level set value b, which is measured by the filling level indicator 8 and sent to the control unit 23. The control unit 23 determines the preset power value for the heating device 12 in order to maintain the anesthetic 2 at a constant temperature of ca. 33° C. by means of the heating coil 11. This temperature is monitored via the temperature sensor 13 and is sent as an actual value signal to the heating device 12. The heating energy for the heating coil 11 is controlled corresponding to the deviation of the anesthetic temperature from the set value of 33° C. A pressure of ca. 700 mbar occurs above the level of the liquid anesthetic 2, so that anesthetic vapor is carried in the outlet line 10 to the metering valve 17. Corresponding to the setting for a desired anesthetic concentration at the control unit 23, the metering valve 17 is actuated in on-off cycles determined by the control unit 23, as a result of which it releases defined quantities of anesthetic into the fresh gas line 18. After a certain operating time, a sufficient amount of anesthetic 2 will have evaporated, so that the liquid level will have dropped to the minimum filling level indicator 14. A corresponding minimum value signal a will then be present in the control unit 23, and this control unit will send a switching impulse to the supply unit 7, which is also an on-off solenoid valve that opens on a control command and opens the supply line 5. The compressed gas delivered from the compressed gas source 4 through the compressed gas line 3 generates so much excess pressure that the anesthetic 2 will be pressed from the reservoir 1 into the supply line 5, passed through the opened valve 7, and delivered into the intermediate container 6 until the level of the liquid anesthetic 2 reaches the filling level indicator 8. When it is reached, the solenoid valve 7 is closed by a corresponding control operation performed by the control unit 23, and the delivery of the anesthetic 2 from the reservoir 1 will be interrupted. If the filling level indicator 8 is defective due to a malfunction, and the level of the liquid anesthetic 2 in the intermediate container 6 has risen to the maximum filling level indicator 15, the solenoid valve 7 will also be closed by a corresponding control signal c sent to the control unit 23. As an additional safety measure, the float valve 16 on the outlet line 10 prevents liquid anesthetic from entering the fresh gas line 18, should the maximum filling level indicator 15 be defective as well. In the case of normal operation, the float valve 16 opens the admission opening of the outlet line 10 into the intermediate container 6, so that gaseous anesthetic is able to flow unhindered into the outlet line 10. The control unit 23 calculates the amount of anesthetic 2 consumed during one unit time from the number of filling cycles between the minimum filling level indicator 14 and the filling level indicator 8. This calculated value is sent to the comparison unit 24. At the same time, the metering control 21 redundantly calculates—by means of the flow sensor 20 and the concentration set value 20 entered—the quantity of gaseous anesthetic needed to produce the necessary anesthetic concentration in the fresh gas line 18. The value of the amount of anesthetic calculated by the metering control 21 is also sent to the comparison unit 24. If the two calculated values agree, metering will be continued by the metering control 21 without change by correspondingly actuating the metering valve 17 on the basis of the pressure value determined by the pressure sensor 9 and the flow measured in the carrier gas line 18 in order to deliver the amount of gaseous anesthetic needed to maintain the required anesthetic concentration in the fresh gas line 18. However, if the quantity values in the comparison unit 24 deviate from a preset difference, the metering valve 17 and the solenoid valve 7 will be closed via a corresponding shutoff signal from the comparison unit 24, so that the supply line 15 and the outlet line 10 will be interrupted, and the temperature for the heating coil 11 is immediately reduced by the heating device 12.

What is claimed is:

1. A metering device for a liquid anesthetic, comprising:
    a liquid anesthetic reservoir including a container with an amount of liquid anesthetic;
    a fresh gas line providing a supply of gas to a patient breathing system;
    a feed line;
    a heatable intermediate container for maintaining anesthetic under pressure, said heatable intermediate container being connected to said reservoir via said feed line;
    an outlet line connected to said heatable intermediate container for removing anesthetic in a gaseous state from said heatable intermediate container and for carrying anesthetic in a gaseous state to said fresh gas line for mixing with said supply of gas providing a fresh gas anesthetic gas mixture to the breathing system;
    a metering valve connected to said outlet line for metering gaseous anesthetic to said fresh gas line to control a percentage of anesthetic gas in said fresh gas anesthetic gas mixture;
    supply means connected to said feed line for allowing liquid anesthetic to flow from said reservoir to said heatable intermediate container for supplying said heatable intermediate container with liquid anesthetic;
    control means for activating said supply means to fill said heatable intermediate container with liquid anesthetic to a predetermined set value of a liquid anesthetic filling level; and
    heating means for heating liquid anesthetic in said intermediate container to a temperature to achieve a predetermined gaseous anesthetic pressure above said liquid anesthetic filling level.

2. A metering device according to claim 1, further comprising a filling level indicator to sense said liquid anesthetic filling level and a filling level signal line, said filling level indicator being connected to said control means for sending a filling level set value to said control means via said filling level signal line.

3. A metering device according to claim 1, further comprising: a minimum filling level indicator and a minimum value signal line, said minimum filling level indicator detecting a filling level below a minimum filling level and sending a minimum value signal to said control means over said minimum value signal line, said control means, upon receiving said minimum value signal, actuating said supply means until said filling level set value is attained.

4. A metering device according to claim 1, further comprising: a maximum filling level indicator and a maximum value signal line, said maximum filling level indicator generating a maximum value signal which is sent over a signal line to said control means, said maximum value signal indicating that a maximum filling level is present, said control means closing said supply means upon receiving said maximum value signal.

5. A metering device according to claim 1, further comprising: metering control means for detecting a flow in said fresh gas line by means of a flow sensor, detecting vapor pressure of said gaseous anesthetic in said intermediate container by means of a pressure sensor and determining switching cycles of said metering valve based on a calculated quantity of anesthetic to be metered in order to reach a predetermined anesthetic concentration set value.

6. A metering device according to claim 5, further comprising a filling level indicator to sense said liquid anesthetic filling level and a filling level signal line, said filling level indicator being connected to said control means for sending a filling level set value to said control means via said filling level signal line and a minimum filling level indicator and a minimum value signal line, said minimum filling level indicator detecting a filling level below a minimum filling level and sending a minimum value signal to said control means over said minimum value signal line, said control means, upon receiving said minimum value signal, actuating said supply means until said filling level set value is attained, said control means calculating an amount of anesthetic consumed based on a number of filling cycles per time between said minimum filling level indicator and said filling level indicator and comparing said amount of anesthetic consumed with a quantity of anesthetic determined by said metering control means and closing said supply unit and said metering valve in a case of deviation between set amounts exceeding a predetermined difference value and switches off said heating device.

7. A metering device for liquid anesthetic boiling at room temperature, comprising: a liquid anesthetic reservoir including a container with an amount of liquid anesthetic; a fresh gas line providing a supply of gas to a patient breathing system; a heatable intermediate container for maintaining anesthetic under pressure; a feed line connecting said liquid anesthetic reservoir to said heatable intermediate container; supply means connected to said feed line for supplying liquid anesthetic from said liquid anesthetic reservoir to said heatable intermediate container; an outlet line connected to said heatable intermediate container for removing anesthetic in a gaseous state from said heatable intermediate container and for carrying anesthetic in a gaseous state to said fresh gas line for mixing with said supply of gas providing a fresh gas anesthetic gas mixture to the breathing system; a metering valve connected to said outlet line for metering gaseous anesthetic to said fresh gas line to control a percentage of anesthetic gas in said fresh gas anesthetic gas mixture; control means for activating said supply means to fill said intermediate container with a liquid anesthetic to maintain liquid anesthetic within said intermediate container above a predetermined minimum filling level; and heating means for heating liquid anesthetic in said intermediate container to a temperature to achieve a predetermined gaseous anesthetic pressure above said liquid anesthetic.

8. A metering device according to claim 7, further comprising: a desired filling level indicator to sense liquid anesthetic at or above a desired liquid anesthetic filling level, a desired filling level signal line, said filling level indicator being connected to said control means for sending a desired filling level signal to said control means via said filling level signal line; a minimum filling level indicator and a minimum value signal line, said minimum filling level indicator detecting a filling level below said minimum filling level and sending a minimum value signal to said control means over said minimum value signal line, said control means, upon receiving said minimum value signal, actuating said supply means until said desired filling level is attained; metering control means for detecting a flow in said fresh gas line by means of a flow sensor, detecting vapor pressure of said gaseous anesthetic in said intermediate container by means of a pressure sensor and determining switching cycles of said metering valve based on a calculated quantity of anesthetic to be metered in order to reach a predetermined anesthetic concentration set value; said control means calculating an amount of anesthetic consumed based on a number of filling cycles per time between said minimum filling level indicator and said desired filling level indicator and comparing said amount of anesthetic consumed with a quantity of anesthetic determined by said metering control means.

9. A metering device for a liquid anesthetic, comprising: a liquid anesthetic reservoir including a container with an amount of liquid anesthetic; a fresh gas line providing a supply of gas to a patient breathing system; a heatable intermediate container for maintaining anesthetic under pressure; a feed line connecting said liquid anesthetic reservoir to said heatable intermediate container; an outlet line connected to said heatable intermediate container and connected to said fresh gas line for removing anesthetic in a gaseous state from said heatable intermediate container and for carrying anesthetic in a gaseous state to said fresh gas line for mixing with said supply of gas providing a fresh gas anesthetic gas mixture to the breathing system; metering means connected to said outlet line for metering gaseous anesthetic to said fresh gas line to control a percentage of anesthetic gas in said fresh gas anesthetic gas mixture; supply means connected to said feed line for supplying said heatable intermediate container with liquid anesthetic from said liquid anesthetic reservoir; control means for activating said supply means to fill said heatable intermediate container with liquid anesthetic to provide liquid anesthetic up to a liquid anesthetic filling level; and heating means for heating liquid anesthetic in said intermediate container to a temperature to achieve anesthetic in a gaseous state, at a predetermined gaseous anesthetic pressure, above said liquid anesthetic filling level.

10. A metering device according to claim 9, further comprising: a liquid anesthetic filling level indicator to sense liquid anesthetic at or above a said liquid anesthetic filling level, a filling level signal line, said liquid anesthetic filling level indicator being connected to said control means for sending a filling level signal to said control means via said filling level signal line; a minimum filling level indicator and a minimum value signal line, said minimum filling level indicator detecting a filling level below said minimum filling level and sending a minimum value signal to said control means over said minimum value signal line, said control means, upon receiving said minimum value signal, actuating said supply means until said filling level is attained; metering control means for detecting a flow in said fresh gas line by means of a flow sensor, detecting vapor pressure of said gaseous anesthetic in said intermediate container by means of a pressure sensor and determining switching cycles of said metering valve based on a calculated quantity of anesthetic to be metered in order to reach a predetermined anesthetic concentration set value; said control means calculating an amount of anesthetic consumed based on a number of filling cycles per time between said minimum filling level indicator and said liquid anesthetic filling level indicator and comparing said amount of anesthetic consumed with a quantity of anesthetic determined by said metering control means.

* * * * *